United States Patent
Schonemann et al.

(10) Patent No.: US 9,029,615 B2
(45) Date of Patent: May 12, 2015

(54) ENERGY EFFICIENT METHOD AND APPARATUS FOR THE EXTRACTION OF LOWER ALCOHOLS FROM DILUTE AQUEOUS SOLUTION

(71) Applicants: Phasex Corporation, Lawrence, MA (US); DynaSep Inc., Wilmington, DE (US)

(72) Inventors: Hans Schonemann, Newburyport, MA (US); Brian J. Waibel, Kenneth Square, PA (US); Val Krukonis, Lexington, MA (US)

(73) Assignees: DynaSep Inc., Wilmington, DE (US); Phasex Corporation, Lawrence, MA (US)

( * ) Notice: Subject to any disclaimer, the term of this patent is extended or adjusted under 35 U.S.C. 154(b) by 190 days.

(21) Appl. No.: 13/801,901

(22) Filed: Mar. 13, 2013

(65) Prior Publication Data

US 2014/0066669 A1 Mar. 6, 2014

Related U.S. Application Data

(60) Provisional application No. 61/697,003, filed on Sep. 5, 2012.

(51) Int. Cl.
*C07C 29/86* (2006.01)
*C07C 29/80* (2006.01)

(52) U.S. Cl.
CPC ............... *C07C 29/86* (2013.01); *C07C 29/80* (2013.01)

(58) Field of Classification Search
CPC .......... C07C 29/86; C07C 29/80; C07C 29/88
USPC .................................. 568/913, 918
See application file for complete search history.

(56) References Cited

U.S. PATENT DOCUMENTS

| | | |
|---|---|---|
| 2,188,051 A | 1/1940 | Lantz |
| 2,631,966 A | 3/1953 | Francis |
| 3,939,281 A | 2/1976 | Schwengers |
| 3,969,196 A | 7/1976 | Zosel |
| 4,124,528 A | 11/1978 | Modell |
| 4,346,241 A | 8/1982 | Feldman |
| 4,379,028 A | 4/1983 | Berg |
| 4,409,406 A | 10/1983 | Feldman |
| 4,454,358 A | 6/1984 | Kummer |
| 4,455,198 A | 6/1984 | Zudkevitch |
| 4,466,923 A | 8/1984 | Friedrich |
| 4,490,405 A | 12/1984 | von Horst |
| 4,492,808 A | 1/1985 | Hagen |
| 4,508,928 A | 4/1985 | Victor |
| 4,517,298 A | 5/1985 | Tedder |
| 4,520,213 A | 5/1985 | Victor |
| 4,578,525 A | 3/1986 | Brueckner |
| 4,624,417 A | 11/1986 | Gangi |
| 4,692,432 A | 9/1987 | Tedder |
| 4,749,495 A | 6/1988 | Schmidt |
| 4,769,112 A | 9/1988 | Wheldon |
| 4,770,780 A | 9/1988 | Moses |
| 4,842,693 A | 6/1989 | Wheldon |
| 4,865,973 A | 9/1989 | Kollerup |
| 4,877,530 A | 10/1989 | Moses |
| 4,956,052 A | 9/1990 | Hirata |
| 5,013,447 A | 5/1991 | Lee |
| 5,028,240 A | 7/1991 | Moore |
| 5,036,005 A | 7/1991 | Tedder |
| 5,084,142 A | 1/1992 | Berg |
| 5,085,739 A | 2/1992 | Berg |
| 5,160,044 A | 11/1992 | Tan |
| 5,215,902 A | 6/1993 | Tedder |
| 5,284,983 A | 2/1994 | Muto |
| 5,349,084 A | 9/1994 | Shishikura |
| 5,354,912 A | 10/1994 | Hwan |
| 5,663,454 A | 9/1997 | Preston |
| 5,718,937 A | 2/1998 | Heidlas |
| 5,932,101 A | 8/1999 | Kanel |
| 6,106,720 A | 8/2000 | Kanel |
| 6,569,640 B1 | 5/2003 | Castor |
| 7,186,796 B2 | 3/2007 | Krukonis |
| 7,537,700 B2 | 5/2009 | Kanda |
| 8,101,808 B2 | 1/2012 | Evanko |
| 8,263,814 B2 | 9/2012 | Waibel |
| 8,409,834 B2 | 4/2013 | Burlew |
| 2003/0108493 A1 | 6/2003 | Henry |
| 2009/0171129 A1 | 7/2009 | Evanko |
| 2010/0151098 A1 | 6/2010 | Catchpole |
| 2010/0160659 A1 | 6/2010 | Catchpole |
| 2011/0162953 A1 | 7/2011 | Xu |
| 2011/0162954 A1 | 7/2011 | Xu |

FOREIGN PATENT DOCUMENTS

| | | |
|---|---|---|
| CN | 1560008 A | 1/2005 |
| DE | 4041097 | 6/1992 |
| DE | 10200226 | 8/2003 |
| EP | 1122259 A | 8/2001 |
| JP | 62029988 | 2/1987 |
| JP | 63162636 | 7/1988 |
| WO | 2005/075614 A | 8/2005 |
| WO | 2008/147705 | 12/2008 |
| WO | 2010/046619 A | 4/2010 |

OTHER PUBLICATIONS

Athanassios Z, et al., "Multiphase High Pressure Equilibria in Ternary Aqueous Systems," FluidPhase Equilibria, 29 (1986) 525-534.
Ennis, et al., "Continuous Product Recovery by In-Situ Gas Stripping/Condensation During Solvent Production From Whey Permeate Using *Clostridium acetobutylicum*," Biotechnology Letters, vol. 8, No. 10 (1986) 725-730.
Laitinen and Kaunisto, "Supercritical fluid extraction of 1-butanol from aqueous solutions," Journal of Supercritical Fluids, 15 (1999) 245-252.

(Continued)

*Primary Examiner* — Elvis O Price
(74) *Attorney, Agent, or Firm* — Greenblum & Bernstein, P.L.C.

(57) ABSTRACT

The present invention relates to the energy efficient and selective extraction of dilute concentrations of C2-C6 alcohols from an aqueous solution using liquid phase dimethyl ether.

33 Claims, 4 Drawing Sheets

(56) References Cited

OTHER PUBLICATIONS

Maddox, et al., "Production of Acetone-Butanol-Ethanol from Concentrated Substrates Using *Clostridium acetobutylicum* in an Integrated Fermentation-Product Removal Process," Process Biochemistry vol. 30, No. 3, (1995) pp. 209-215.

Qureshi and Blaschek, "Recovery of butanol from fermentation broth by gas stripping," Renewable Energy 22 (2001) 557-564.

Groot et al., "Butanol Recovery from Fermentations by Liquid-Liquid Extraction and D Membrane Solvent Extractions," 1990, Bioprocess Engineering, 5, pp. 203-216.

Mehta et al., "A Novel Extraction Process for Separating Ethanol and Water," Ind. Eng. Chern. Process Des. Dev., 1985, 24, 558-560.

Munson et al., "Factors Influencing Solvent Selection for Extraction of Ethanol from Aqueos Solutions," Ind. Eng. Chem. Process Des. Dev.,1984, 23,109-115.

Offeman, et al., "Solvent Extraction of Ethanol from Aqueous Solutions Using Biobased Oils, Alcohols, and Esters," JAOCS, vol. 83, No. 2, (2006), 153-157.

ENERGY EFFICIENT METHOD AND APPARATUS FOR THE EXTRACTION OF LOWER ALCOHOLS FROM DILUTE AQUEOUS SOLUTION

CROSS-REFERENCE TO RELATED APPLICATIONS

This application claims the benefit under 35 U.S.C. §119 (e) of U.S. Provisional Application No. 61/697,003, filed on Sep. 5, 2012, which is hereby incorporated herein by reference in its entirety for all purposes.

FIELD OF THE INVENTION

The present invention relates to the energy efficient and selective extraction of C2-C6 alcohols from an aqueous solution, particularly aqueous solutions containing the alcohol in dilute or low concentrations, for example, fermentation broths.

BACKGROUND OF THE INVENTION

The notion of using a liquid solvent to extract lower alcohols, e.g., ethanol, from an aqueous solution has been pursued since the early 1980s. For example, in 1984, Munson and King published "Factors Influencing Solvent Selection for Extraction of Ethanol from Aqueous Solutions," Industrial and Engineering Chemistry Process Design and Development, 23, p 109-115. Munson and King examined solvents and solvent mixtures for the extraction of ethanol from dilute aqueous solutions. Results were tabulated on the basis of capacity, as represented by the distribution coefficient, and selectivity, as represented by the separation factor. Munson and King showed that an increasing distribution coefficient generally correlates with a decreasing separation factor. Thus, as the solvent become more effective for extracting ethanol, the solvent, unfortunately, becomes less effective for rejecting the water.

Previously disclosed methods of using an oil to extract ethanol from a dilute aqueous solution have proven to be energetically and economically inefficient. For example, Metha and Fraser, "A Novel Extraction Process for Separating Ethanol and Water," Industrial and Engineering Chemistry Process Design and Development, 24, 1985, p 556-560 detail a method to use light paraffin oil to extract ethanol from water. Their method leverages the ternary phase behavior of ethanol-water-paraffin oil system. The proposed process scheme requires process temperatures in the range from 30° C. to 115° C. The report does not provide the optimum process conditions. Ethanol's boiling point is 78° C. Furthermore, in order to have favorable energy input into the process, the process requires that paraffin oil travel with the discharged ethanol. Because paraffin oil is more valuable than ethanol, it is not clear that the proposed process has an economic advantage.

Numerous published methods for the extraction of ethanol require a distillation step to remove ethanol from water, which is energetically and economically inefficient, and an unnecessary additional step. For example, U.S. Pat. Nos. 4,409,406; 4,865,973; 4,770,780; 5,036,005; and 5,215,902 each disclose processes for the extraction of ethanol that require a distillation step to remove ethanol from water.

Others have also proposed using carbon dioxide as a primary extractant of ethanol from an aqueous solution. However, these methods are limited by the distribution coefficient between ethanol-water and $CO_2$ that has been measured to be on the order of 0.1 by numerous researchers, e.g., Krukonis (FIG. 8.11, p. 173, McHugh, M., Krukonis, V., Supercritical Fluid Extraction, 2nd Ed., Butterworth-Heinemann, 1994). These processes have no energy advantage over a traditional binary distillation process. See, for example, U.S. Pat. Nos. 4,842,693; 5,160,044; and 4,770,780.

SUMMARY OF THE INVENTION

The present invention provides energetically efficient and economically viable methods and systems for the concentration of a C2-C6 alcohol from dilute aqueous solutions.

In one aspect, the invention provides an energetically efficient method for concentrating a C2-C6 alcohol from a dilute alcohol-water solution. In some embodiments, the methods comprise:

a) mixing the dilute alcohol-water solution with liquid phase dimethyl ether (DME), wherein the distribution coefficient for the alcohol in a mixture of the DME and the alcohol-water solution favors the transfer of the alcohol from the alcohol-water solution to the DME, thereby yielding a solution comprising a first phase and a second phase, the first phase comprising alcohol-saturated DME and the second phase comprising the dilute alcohol-water solution (i.e., aqueous solution comprising unextracted alcohol or raffinate), thereby extracting a portion of the alcohol from the alcohol-water solution into the DME;

b) separating the first phase comprising alcohol-saturated DME and the second phase comprising the dilute alcohol-water solution;

c) vaporizing the liquid phase DME in the first phase to vapor phase DME, thereby releasing the alcohol from the DME, yielding a concentrated alcohol-water solution;

d) recovering the vapor phase DME by condensing to liquid phase, wherein the vaporizing and the condensing of the DME is driven by a refrigerant circuit; and e) repeating steps a)-d), wherein the DME recovered in step d) is mixed with the dilute alcohol-water solution in step a). The concentrated alcohol-water solution comprises a greater alcohol concentration than the alcohol concentration in the starting alcohol-water solution.

In a further aspect, the invention provides methods for concentrating a C2-C6 alcohol from a dilute alcohol-water solution. In some embodiments, the methods comprise:

a) mixing the dilute alcohol-water solution comprising less than 10 wt. % alcohol with liquid phase dimethyl ether (DME), wherein the distribution coefficient for the alcohol in a mixture of the DME and the alcohol-water solution favors the transfer of the alcohol from the alcohol-water solution to the DME, thereby yielding a solution comprising a first phase and a second phase, the first phase comprising alcohol-saturated DME and the second phase comprising the dilute alcohol-water solution, thereby extracting a portion of the alcohol from the alcohol-water solution into the DME;

b) separating the alcohol-saturated DME phase and the alcohol-water solution phase;

c) vaporizing the DME to vapor phase, thereby releasing the alcohol from the DME, yielding an alcohol-water solution of greater alcohol concentration than the alcohol concentration in the starting alcohol-water solution;

d) recovering the vapor phase DME by condensing to liquid phase; and e) repeating steps a)-d), wherein the DME recovered in step d) is mixed with the dilute alcohol-water solution in step a). In some embodiments, steps a)-d) are repeated 10 or fewer times, for example, 10, 9, 8, 7, 6, 5, 4, 3 or 2 iterations.

In a related aspect, the invention provides methods for concentrating a C2-C6 alcohol from a dilute alcohol-water solution. In some embodiments, the methods comprise:

a) mixing the dilute alcohol-water solution with liquid phase dimethyl ether (DME), wherein the distribution coefficient for the alcohol in a mixture of the DME and the alcohol-water solution favors the transfer of the alcohol from the alcohol-water solution to the DME, thereby yielding a solution comprising a first phase and a second phase, the first phase comprising alcohol-saturated DME and the second phase comprising the dilute alcohol-water solution, thereby extracting a portion of the alcohol from the alcohol-water solution into the DME;

b) separating the first phase and the second phase; and c) converting the liquid-phase DME to vapor phase, thereby releasing the alcohol from the DME, yielding a concentrated alcohol-water solution.

With respect to the embodiments of the methods, in some embodiments, the methods further comprise the step of isolating the alcohol-water solution released from the DME, e.g., when the alcohol-water solution has an alcohol concentration that is greater than the alcohol concentration of the feedstock dilute alcohol solution.

In some embodiments, steps a)-d) are repeated 10 or fewer times, for example, 10, 9, 8, 7, 6, 5, 4, 3 or 2 iterations. In various embodiments, the steps are performed as a continuous flow process.

In some embodiments, the mixing of step a) is performed in one or more countercurrent extraction stages, for example, in 2, 3, 4, 5, 6, 7, 8, 9, 10 or more countercurrent extraction stages.

In some embodiments, the DME is recovered by vapor recompression. In some embodiments, the methods further comprise the step of condensing and reusing the vaporized DME.

In some embodiments, the vaporizing and the condensing of the DME is driven by a refrigerant circuit. In some embodiments, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R 227ea, R 236ea, R 245ca, R-365mfc, RC318, R 406a, R-410a, R-414a, R-500, R-502, R-503, R-1301 and ammonia. In some embodiments, the refrigerant in the refrigerant circuit is R-134a.

In various embodiments, the unconcentrated or feedstock dilute alcohol-water solution comprises from about 0.1 wt. % to about 10.0 wt. % alcohol, for example, from about 0.1 wt. % to about 5.0 wt. % alcohol, for example, from about 0.1 wt. % to about 3.0 wt. % alcohol, for example, at least about 0.1 wt. % alcohol and less than about 0.2 wt. %, 0.3 wt. %, 0.4 wt. %, 0.5 wt. %, 0.6 wt. %, 0.7 wt. %, 0.8 wt. %, 0.9 wt. %, 1.0 wt. %, 1.5 wt. %, 2.0 wt. %, 2.5 wt. %, 3.0 wt. %, 3.5 wt. %, 4.0 wt. %, 4.5 wt. %, 5.0 wt. %, 5.5 wt. %, 6.0 wt. %, 6.5 wt. %, 7.0 wt. %, 8.0 wt. %, 9.0 wt. % or 10.0 wt. % alcohol. In some embodiments, the unconcentrated or feedstock dilute alcohol-water solution is a fermentation beer or fermentation broth. In various embodiments, the unconcentrated or feedstock dilute alcohol-water solution comprises from 2-4 wt. % ethanol. In various embodiments, the unconcentrated or feedstock dilute alcohol-water solution comprises about 1-2 wt. % butanol (BuOH). In some embodiments, the unconcentrated or feedstock dilute alcohol-water solution is a *Clostridium* fermentation broth. In various embodiments, the feedstock dilute alcohol-water solution comprises cellular biomass in suspension.

In various embodiments, the concentration of the concentrated alcohol-water solution is at least about 2-fold, 3-fold, 4-fold, 5-fold, 10-fold, 15-fold, or more, of the concentration of the alcohol in the unconcentrated or feedstock dilute alcohol-water solution. In some embodiments, the concentration of the concentrated alcohol-water solution is at least about 7.0 wt. %, for example, at least about 8.0 wt. %, 9.0 wt. %, 10.0 wt. %, 15.0 wt. %, 20.0 wt. %, 25.0 wt. %, 30.0 wt. % alcohol.

Generally, concentration using DME does not comprise distillation. In various embodiments, the alcohol is further concentrated, e.g., by distillation, once the concentration of the alcohol released from the DME is greater than a threshold or target alcohol concentration, e.g., greater than about 7 wt. %, for example, greater than about 8.0 wt. %, 9.0 wt. % or 10.0 wt. %.

In various embodiments, the method is performed a temperature in the range of about 20° C. to about 150° C., for example, in the range of about 20° C. to about 100° C., for example in the range of about 20° C. to about 50° C. In some embodiments, the method is performed at ambient temperature, e.g., in the range of about 20° C. to about 35° C. In some embodiments, the method is performed at fermentation temperature. For example, for certain organisms, fermentation temperature is in the range of about 35° C. to about 40° C., e.g., about 35° C., 36° C., 37° C., 38° C., 39° C. or 40° C.

In various embodiments, the method is performed at a pressure in the range of about 3 bar to about 50 bar, for example, in the range of about 3 bar to about 10 bar, for example, in the range of about 5 bar to about 10 bar, for example, about 3 bar, 4 bar, 5 bar, 6 bar, 7 bar, 8 bar, 9 bar or 10 bar.

In some embodiments, the DME is mixed with the feedstock the unconcentrated or feedstock dilute alcohol-water solution at a solvent-to-feedstock ratio in the range of about 0.5 to about 2.0, for example, from about 1.0 to about 1.5, for example, at a solvent-to-feedstock ratio of about 0.5, 0.75, 1.0, 1.25, 1.5, 1.75, or 2.0.

In some embodiments, the energy input for alcohol concentration is less than 3000 BTU/Lb alcohol recovered, for example, less than 2900 BTU/Lb, 2800 BTU/Lb, 2700 BTU/Lb, 2600 BTU/Lb, 2500 BTU/Lb, 2400 BTU/Lb, 2300 BTU/Lb, 2200 BTU/Lb, 2100 BTU/Lb, 2000 BTU/Lb, 1900 BTU/Lb, 1800 BTU/Lb, 1700 BTU/Lb, 1600 BTU/Lb, 1500 BTU/Lb, 1400 BTU/Lb, 1300 BTU/Lb, 1200 BTU/Lb, 1100 BTU/Lb, 1000 BTU/Lb alcohol recovered.

In various embodiments, at least about 60%, for example, at least about 70%, 75%, 80%, 85%, 90%, 95%, or more, of the alcohol in the feedstock dilute aqueous solution is concentrated and recovered.

In various embodiments, the C2-C6 alcohol is selected from ethanol, a propanol, a butanol, a pentanol and a hexanol. In some embodiments, the alcohol is a C2-C5 alcohol. In some embodiments, the alcohol is ethanol.

In some embodiments, the alcohol is a propanol or C3 alcohol. In some embodiments, the propanol is selected from the group consisting of 1-propanol and 2-propanol.

In some embodiments, the alcohol is a butanol or C4 alcohol. In some embodiments, the butanol is selected from the group consisting of 1-butanol, 2-butanol, tert-butanol (2-methyl-2-propanol), and iso-butanol (2-methyl-1-propanol).

In some embodiments, the alcohol is a pentanol or C5 alcohol. In some embodiments, the pentanol is selected from the group consisting of 1-pentanol, 2-pentanol, 3-pentanol, 2-methyl-1-butanol, 3-methyl-1-butanol, 2-methyl-2-butanol, 3-methyl-2-butanol, and 2,2-dimethyl-1-propanol.

In some embodiments, the alcohol is a hexanol or C6 alcohol. In some embodiments, the hexanol is selected from the group consisting of 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, and 2-ethyl-1-butanol.

In various embodiments, the unextracted alcohol and residual DME in the second phase is returned to the feedstock dilute aqueous solution, e.g., wherein the feedstock dilute aqueous solution is a fermentation broth. In some embodiments, the fermentation beer or fermentation broth comprises up to about 3 wt. % DME.

In various embodiments, the DME, or analogs thereof, is not a polyoxaalkane, a glycol or a glyme.

DEFINITIONS

The term "alcohol component" refers to a straight or branched, saturated, radical having 2-6 carbon atoms and one or more hydroxy groups. The alkyl portion of the alcohol component can be ethyl, methyl, dimethyl, propyl, butyl, pentyl, iso-propyl, iso-butyl, sec-butyl, tert-butyl, etc. Alcohol components useful in the present invention include, but are not limited to, ethanol, propanol, isopropanol, butanol, isobutanol, t-butanol and pentanol, among others. One of skill in the art will appreciate that other alcohol components are useful in the present invention.

The terms "extraction," "extracting" and "extracted" interchangeably refer to the process of drawing one component of a mixture into another mixture. In the present invention, the alcohol of the alcohol-water solution is first drawn from the alcohol-water solution into the dimethyl ether ("DME").

The phrase "converting to vapor phase" refers to the step of altering the temperature and pressure of the DME to change the phase of the DME from liquid phase or near supercritical phase to the vapor phase.

The term "liquid phase" refers to DME under the appropriate temperature and pressure conditions in order to form a liquid phase. Provided the temperature and pressure are below the critical point for DME (127.15° C. and 53.405 bar), the liquid phase of DME can be achieved through pressure alone, temperature alone, or through a combination of temperature and pressure. One of skill in the art will know what temperature and pressure are appropriate to form the liquid phase of DME.

The term "supercritical phase" refers to DME under the appropriate temperature and pressure conditions in order to form a supercritical phase or near supercritical phase. This exists at a temperature and pressure that exceeds the critical temperature of 127.15° C. and critical pressure of 54.405 bar. One of skill in the art will know what temperature and pressure are appropriate to form the supercritical phase of DME.

The term "subcritical phase" refers to a compound that is maintained at a temperature and/or pressure that is below its critical temperature and/or pressure. A compound maintained in subcritical phase can be in either gas phase or liquid phase, or both (e.g., a dense gas). The critical point of DME is 127° C. and 774.5 psi (53.4 bar; 52.7 atm). In some embodiments, the DME is maintained at a pressure well below its critical pressure, e.g., at a pressure of about 145 psi (10 bar; 9.87 atm) or less.

The term "recycle" refers to the processing of materials so that the materials can be used again. Following extraction of the alcohol and vaporization, the DME is condensed back to the liquid phase and returned to the step of alcohol extraction with DME. The recycling prevents resources from being wasted, reduces the consumption of raw materials and reduces energy usage.

The term "reuse" refers to the act of using for a subsequent time, an item that has already been used. In the present invention, the DME used in the extraction is converted to the vapor phase in order to separate the alcohol. The vapor phase DME is recycled via condensation and supplied back to the extraction apparatus, thus being used again to extract additional alcohol from the first solvent.

The term "countercurrent column" refers to a column in which liquid-liquid separation occurs using countercurrent techniques. One of skill in the art will appreciate the countercurrent techniques are useful in the methods of the present invention.

The term "distribution coefficient" refers to the ratio of concentrations of all forms of a compound (ionized and unionized) in the two phases of a mixture of two immiscible solvents at equilibrium. See, Leo, et al., Chem Rev (1971) 71(6):525-616. The distribution coefficient can be used as a measure of how hydrophilic or hydrophobic a chemical substance is. The distribution coefficient describes the pH-dependent hydrophobicity of compounds, and is related to P (the partition coefficient), which describes the hydrophobicity of neutral (i.e., unionized) compounds only. The distribution coefficient can be symbolized as "K" or "D." D (or K) is the ratio of the sum of concentrations of the solute's (e.g., alcohol) various forms in one solvent, to the sum of the concentrations of the solute's forms in the other solvent, where the units of the concentration can be weight percent, mole percent, or g/mL, and can be calculated by the following equation:

$$D_{organic/water} = [\text{solute}]_{organic}/[\text{solute}]_{water}$$

The distribution coefficient can be measured using any method known in the art. Exemplified methods include (i) the shake flask or tube method and (ii) high performance liquid chromatography (HPLC) or gas chromatography (GC). In the shake flask method, the solute in question is diluted or dissolved to equilibrium in equal volumes of a mixture of organic phase solvent and water phase solvent, then the concentration of the solute in each solvent is measured, for example, by HPLC, GC, UV/VIS spectroscopy. In HPLC, the D of a solute can be determined by correlating its retention time with similar compounds with known D values.

The term "separation factor" refers to a measure of the fold-difference or ratio of two different distribution coefficients in self-consistent units. A separation factor can be symbolized as "α" and is calculated by dividing one distribution ratio by another. The separation factor is a measure of the ability of a system to separate two solutes.

The phrase "continuous flow process" refers to a process having constant input and output. For example, when a fermentation is not rendered toxic by the solvent, the fermentation will continuously produce alcohol, which can be siphoned into an extraction process. The siphoning off of alcohol maintains a low concentration of alcohol allowing fermentation to continue indefinitely. A continuous flow process is in contrast to a process that requires batch or discontinuous processing.

A "dilute" aqueous solution as used herein means a solution containing the C2-C6 alcohol at a concentration below the solubility limit of the C2-C6 alcohol in the solution. Concentration can be expressed in a variety of different units, e.g. weight or volume percent, molar concentration, molal concentration or alcohol/water w/w of v/v ratio. Unless specified otherwise, however, the concentrations are presented here as weight percent. In some embodiments, the phrase "dilute alcohol-water solution" refers to a solution comprising water and about 10 wt. % or less of one or more C2-C6 alcohols, for example, in the range of about 0.1 wt. % to about 10 wt. %, for example, about 10%, 9%, 8%, 7%, 6%, 5%, 4%, 3%, 2%, 1%, 0.8%, 0.5%, 0.3%, 0.2% or 0.1% wt. %, or less, of alcohol.

The term "fermentation" or "fermentation process" is defined as a process in which a biocatalyst is cultivated in a culture medium containing raw materials, such as feedstock and nutrients, wherein the biocatalyst converts raw materials, such as a feedstock, into products. The biocatalyst may be any microorganism capable of converting a selected feedstock to a desired C3-C6 alcohol, e.g., a yeast or bacterium. Any feedstock that contains a fermentable carbon source is suitable for the present invention.

The terms fermentation broth and fermentation medium are synonymous. Unless explicitly noted, the term fermentation broth should be construed to include both fermentation broth containing micro-organisms as well as fermentation broth which does not contain microorganisms.

A "solution of greater alcohol concentration" refers to a solution of alcohol that has been subjected to an extraction process of the invention with a detectably greater concentration of alcohol in comparison to the feedstock solution of alcohol. Determination of alcohol concentrations in an alcohol solution (e.g., an alcohol-water solution) are well known in the art. Alcohol concentrations can be determined using any method known in the art, including for example, gas chromatography or Karl-Fischer titration analysis. The amount of change in concentration will typically depend on the concentration of alcohol in the feedstock solution. Extraction of a feedstock alcohol-water solution of low alcohol concentration will result in an end product with a relatively larger amount of alcohol concentration. Known assays can detect alcohol concentration changes of at least about 0.1%. Using the extraction methods of the invention, the end product solution can have an alcohol concentration that is at least about 5%, 10%, 20%, 30%, 50%, 1-fold, 2-fold, 3-fold, 4-fold, or more, greater than the feedstock alcohol-water solution.

The phrase "fluid communication" refers to at least two elements that are connected in such a way to allow for the free flow of a fluid medium from the one element to the second element. Two elements can optionally be connected by a controller (e.g., a valve) of the flow of the fluid medium.

The term "consisting essentially of" refers to the extractants expressly identified (i.e., DME) and excludes extractants not expressly identified (e.g., organic solvents).

In the context of performance of method steps, the term "directly" refers to sequentially performed steps excluding intermediary actions not expressly identified. In various embodiments, the methods do not comprise distillation and/or freezing.

DETAILED DESCRIPTION

1. Introduction

Figure 1:
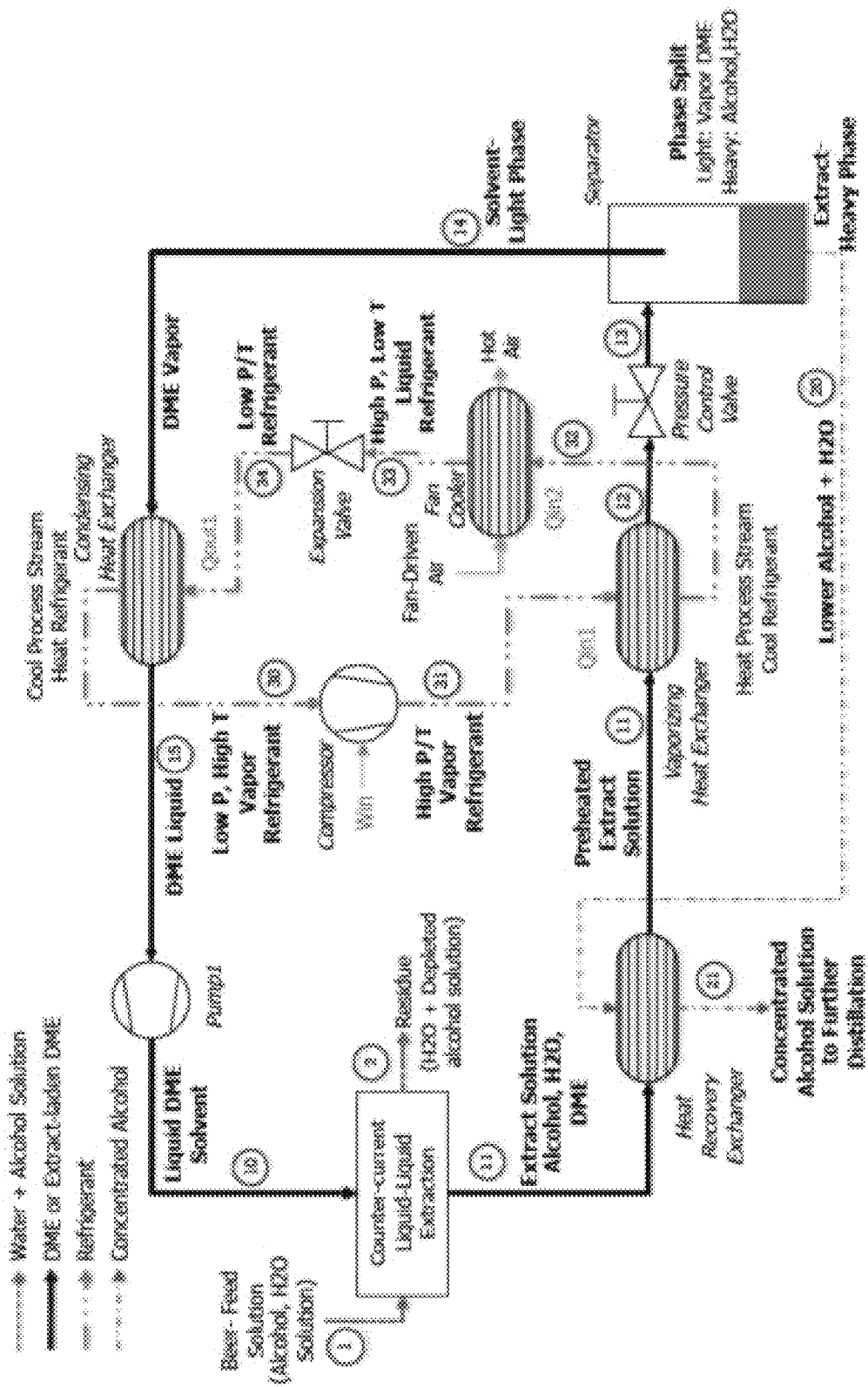
FIG. 1 illustrates a schematic for continuous flow, energy efficient concentration of lower alcohols from aqueous solution using DME liquid-liquid-extraction.

The present invention is based, in part, on the discovery that liquid phase dimethyl ether ("DME") can be used as a solvent to efficiently concentrate low concentrations of C2-C6 alcohols from aqueous solutions. Concentration of dilute concentrations of lower alcohols is achieved by contacting the dilute aqueous solution with a sufficient amount of liquid phase dimethyl ether, which has the characteristics of a favorable distribution coefficient for C2-C6 alcohols between the aqueous solution and the DME solvent and is non-toxic to a fermentation bath. When combined with a lower alcohol-water solution, the DME dissolves a portion of the alcohol present and a more limited portion of the water present, producing a biphasic solution comprising a first phase enriched with DME and alcohol and a second water-rich phase. The DME-alcohol rich phase is separated from the water-rich phase. The pressure and temperature are then adjusted so that the DME can be converted to the vapor phase and the liquid alcohol in the first can be recovered and/or subject for further concentration. This invention provides a means to more energy efficiently separate the dilute C2-C6 alcohols from water (as is typical of a fermentation bath). The methods of the invention can extract lower alcohols from an aqueous solution in an energetically and economically favorable manner and without the need for distillation of alcohol from water.

In preferred embodiments, the methods are performed as a continuous flow process, wherein materials are continuously flowing from one step to the next, or from one element to the next in the present systems. In some embodiments, materials (e.g., the DME as extraction solvent) are recycled and reused. The recycling and reuse of materials provides several energy savings. Additional energy savings derive from the lack of a distillation step or a freezing step in the in the concentration of dilute amounts of alcohol in the aqueous solution. Instead of an energy inefficient process requiring distillation of dilute concentrations of lower alcohols from water, the present invention uses liquid phase DME to extract the alcohol. The DME containing the lower alcohol is then vaporized to separate from the alcohol, followed by condensation of the DME in order to recycle and reuse the DME. The total energy required to achieve the alcohol separation from water is much less than that required by conventional distillation and dehydration via molecular sieve. Accordingly, the methods of the present invention provide an energy efficient process for extracting lower alcohols from a dilute alcohol-water solution.

The methods find use for cellulosic ethanol production. At an ethanol ("EtOH") concentration of approximately 7 wt %, distillation becomes energetically and economically practical. Unfortunately, given the current state of the art in cellulosic ethanol production, it is difficult to convert cellulose to sugar in sufficient quantity to create a beer (dilute ethanol broth) solution greater than 4 wt %. Using DME as a concentrating extraction solvent enables cellulosic ethanol production to proceed with presently existing enzymes and technology without requiring increases in enzymatic efficiency or increases in the solids loading in water. The current art supports solids loading in the range of about 12 wt % with a conversion efficiency of about 60%. The amount of alcohol is about half this amount or 3.6 wt % EtOH (12 wt % solids× 60% conversion efficiency to sugar×50% conversion to EtOH from sugar).

2. Methods for Extracting Lower Alcohols from Dilute Aqueous Solution a. Feedstock

The methods involve mixing a lower alcohol-water solution with liquid phase DME. The alcohol-water solution can be any aqueous solution comprising one or more lower alcohols, e.g, alcohols comprising from 2 to 6 carbons (i.e., C2-C6 alcohols). Illustrative lower alcohols include ethanol, a propanol (i.e., a C3 alcohol), a butanol (i.e., a C4 alcohol) and a pentanol (i.e., a C5 alcohol). In some embodiments, the alcohol is ethanol. In some embodiments, the alcohol is a propanol, e.g., 1-propanol or 2-propanol. In some embodiments, the alcohol is a butanol, e.g., 1-butanol, 2-butanol, tert-butanol (2-methyl-2-propanol), or iso-butanol (2-methyl-1-propanol). In some embodiments, the alcohol is a pentanol, e.g., 1-pentanol, 2-pentanol, 3-pentanol, 2-methyl-1-butanol, 3-methyl-1-butanol, 2-methyl-2-butanol, 3-methyl-2-butanol, or 2,2-dimethyl-1-propanol. In some embodiments, the alcohol is a hexanol, e.g., 1-hexanol, 2-hexanol, 3-hexanol, 2 methyl-1-pentanol, 3-methyl-1-pentanol, 4-methyl-1-pentanol, 2-methyl-2-pentanol, 3 methyl-2-pentanol, 4-methyl-2-pentanol, 2-methyl-3-pentanol, 3-methyl-3-pentanol, 3,3 dimethyl-1-butanol, 2,2-dimethyl-1-butanol, 2,3-dimethyl-1-butanol, 2,3-dimethyl-2-butanol, 3,3-dimethyl-2-butanol, and 2-ethyl-1-butanol.

In some embodiments, the alcohol-water solution is a dilute alcohol solution comprising about 10 wt. % or less of the lower alcohol, for example less than about 10%, 9%, 8%, 7%, 6%, 5%, 4%, 3%, 2%, 1%, 0.9%, 0.8%, 0.7%, 0.6%, 0.5%, 0.4%, 0.3% or 0.2% alcohol and more than about 0.1% alcohol. In some embodiments, the alcohol-water solution has been subjected to at least one iteration of concentration and is being subject to subsequent iterations of concentration.

In various embodiments, the alcohol-water solution can be from fresh or unconcentrated feedstock, for example, from a fermentation broth. Any feedstock that contains a fermentable carbon source is suitable for embodiments of the present invention that include a step of culturing a microorganism. Examples include feedstocks containing polysaccharides, such as starch, cellulose and hemicellulose, feedstocks containing disaccharides, such as sucrose, sugarcane juice and sucrose-containing molasses, and monosaccharides, such as glucose and fructose. Suitable feedstocks include starchy crops, such as corn and wheat, sugarcane and sugar beet, molasses and lignocellulosic material. Suitable feedstocks also include algae and microalgae. Where desired, the feedstock may undergo treatments such as comminution, milling, separation of the carbon source from other components, such as proteins, decrystallization, gelatinization, liquefaction, saccharification, and hydrolysis catalyzed by means of chemical and/or enzymatic catalysts. Such treatment can be conducted prior to fermenting or simultaneously with it, e.g. as in simultaneous saccharification and fermentation. In various embodiments, the feedstock alcohol-water solution can be a fermentation broth or beer, e.g., from the fermentation of fruits, amylaceous grains and tubers (e.g., corn and potatoes), cane sugar, grasses and/or cellulose.

Suitable microorganisms can be selected from naturally occurring microorganisms, genetically engineered microorganisms and microorganisms developed by classical techniques, or a combination thereof. Such microorganisms can include, without limitation, bacteria and fungi (including yeast). For example, suitable bacteria can include those that are capable of alcohol production such as the bacteria of the *Clostridium* species. Examples of these include without limitation, *Clostridium butyricum*, *Clostridium acetobutylicum*, *Clostridium saccharoperbutylacetonicum*, *Clostridium saccharobutylicum* and *Clostridium beijerickii*.

Suitable bacteria and fungi also include those that are capable of hydrolyzing carbohydrates and can be genetically engineered to produce alcohols. Examples include, without limitation, bacteria of the order Clostridiales (e.g. *Butyrovibrio fibrisolvens*), Bacilliales (e.g. *Bacillus circulans*), Actinomycetales (e.g. *Streptomyces cellulolyticus*), Fibrobacterales (e.g. *Fibrobacter succinogenes*), Xanthomonadales (*Xanthomonas* species) and Pseudomonadales (e.g. *Pseudomonas mendocina*) and fungi such as those of the order *Rhizopus, Saccharomycopsis, Aspergillus, Pichia, Schwanniomyces* and *Polysporus*. The fungi may be able to do the conversion aerobically or anaerobically. Examples of anaerobic fungi include, without limitation, *Piromyces* species (e.g. strain E2), *Orpinomyces* species (e.g. *Orpinomyces bovis*), *Neocallimastix* species (*N. frontalis*), *Caecomyce* species, *Anaeromyces* species and *Ruminomyces* species.

As noted above, any microorganism, whether naturally occurring or manmade, that is capable of producing alcohol can be used and the methods of the present invention are not limited to the examples listed here. In some embodiments, the microorganism is viable at temperatures from about 20° C. to about 95° C. Reference to a microorganism being viable at a given temperature or range of temperatures refers to a microorganism being able to survive exposure to such temperatures and subsequently be able to grow and/or produce metabolic products under the same or different conditions. In other embodiments, the microorganism is a temperature resistant microorganism. In other embodiments, the microorganism is a DME resistant microorganism. The term "resistance" is defined as the property of a biocatalyst to have a low rate of inhibition in the presence of increasing concentrations of an inhibitor in the fermentation broth.

The term "tolerance" is defined as the ability of the biocatalyst to maintain its specific productivity at a given concentration of an inhibitor. The term "tolerant" describes a biocatalyst that maintains its specific productivity at a given concentration of an inhibitor. For example, if in the presence of 2% of an inhibitor a biocatalyst maintains the specific productivity that it had at 0 to 2%, the biocatalyst is tolerant to 2% of the inhibitor or has a tolerance to 2% of the inhibitor. The term "tolerance to temperature" is defined as the ability of the biocatalyst to maintain its specific productivity at a given temperature. The term "tolerance to DME" is defined as the ability of the biocatalyst to maintain its specific productivity at a given concentration of DME.

In some embodiments, the microorganism has a productivity of at least about 0.5 g/L per hour of the C3-C6 alcohol in aggregate over the lifetime of a batch fermentation cycle. In some embodiments, the productivity is at least about 1, at least about 1.5, at least about 2.0, at least about 2.5, at least about 3, at least about 3.5, at least about 4.0, at least about 4.5, and at least about 5.0 g/L per hour of the C3-C6 alcohol in aggregate over the lifetime of a batch fermentation cycle. In some embodiments, the productivity ranges from about 0.5 g/L per hour to about 5 g/L per hour of the C3-C6 alcohol over the lifetime of a batch fermentation cycle.

In some embodiments, the feedstock is an acetone-butanol-ethanol (ABE) fermentation broth or beer, e.g., resulting from bacterial fermentation to produce acetone, n-butanol and ethanol from starch. Such ABE solutions are produced by bacteria of the genus *Clostridium*, including *Clostridium acetobutylicum, Clostridium beijerinckii, Clostridium butyricum*, and *Clostridium saccharoperbutylacetonicum*. ABE solutions generally comprise acetone, n-butanol and ethanol in a ratio of about 3-6-1 (i.e., 3 parts acetone, 6 parts butanol and 1 part ethanol), and in dilute concentrations (about 0.2 wt. % acetone, about 0.6 wt % n-butanol, and about 0.1% ethanol).

Preferably, the feedstock is an aqueous solution where the biomass has been substantially removed. Usually, the feedstock is an aqueous solution where solids have been substantially removed.

b. Contacting Feedstock with Dimethyl Ether

The solution comprising dilute concentrations of a lower alcohol is contacted with dimethyl ether (DME) under conditions sufficient to concentrate the alcohol into the DME.

In some embodiments, the alcohol-water solution is contacted with DME that is in subcritical phase, i.e., at a temperature and pressure that is below the critical temperature and pressure for DME. In various embodiments of performing the present methods, the DME can be delivered and maintained at ambient temperature and at a pressure that is well below its critical pressure of about 774.5 psi (53.4 bar; 52.7 atm).

In various embodiments, the methods are performed at a temperature in the range of about 20° C. to about 35° C., for example, about 20° C., 21° C., 22° C., 23° C., 24° C., 25° C., 26° C., 27° C., 28° C., 29° C., 30° C., 31° C., 32° C., 33° C., 34° C. or 35° C. In various embodiments, the methods are performed at a fermentation temperature. For example, for certain organisms, fermentation temperature is in the range of about 35° C. to about 40° C., for example at a temperature of about 35° C., 36° C., 37° C., 38° C., 39° C. or 40° C.

In some embodiments, the DME is delivered and maintained in liquid phase. For example, the DME is delivered and maintained at a pressure at or above the vapor pressure, e.g., above about 85 psi (5.9 bar; 5.8 atm) and below 145 psi (10 bar; 9.87 atm), for example, about 85 psi (5.9 bar; 5.8 atm); 87 psi (6 bar; 5.9 atm); 102 psi (7 bar; 6.9 atm); 116 psi (8 bar; 7.9 atm); 131 psi (9 bar; 8.9 atm); or 145 psi (10 bar; 9.87 atm). In performing the present methods, the DME can be delivered and maintained at ambient temperature and at a pressure that above the vapor pressure and below its critical pressure of about 774.5 psi (53.4 bar; 52.7 atm).

The DME can be added in an amount such that the DME ratio with the dilute aqueous solution feedstock (i.e., solvent-to-feed ratio) is about 2:1 to about 1:1, for example, about 1.5:1 to about 1:1, for example about 2.0:1, 1.9:1, 1.8:1, 1.7:1, 1.6:1, 1.5:1, 1.4:1, 1.3:1, 1.2:1, 1.1:1 or 1.0:1.

The DME can be contacted and mixed with the aqueous solution comprising dilute concentrations of alcohol using any method known in the art. Those of skill will appreciate that the delivery method will be appropriate to the phase of the DME solvent, e.g., liquid, subcritical, or supercritical phase. The DME can be delivered in continuous or batch processing, with sufficient agitation to mix homogeneously with the aqueous solution. In some embodiments, the DME is contacted with the alcohol-water solution in a countercurrent manner. For example, gas-phase DME can be bubbled up through a vertical column through which the aqueous solution is being poured down. In other embodiments, the DME is mixed with the aqueous solution using a mixer, e.g., an in-line mixer.

The DME can be unused or recycled from a previous extraction stage or iteration. In embodiments performing liquid-liquid extraction in a countercurrent column, the DME can be introduced into the base of the column. The column can be adjusted in length and width (e.g., internal diameter) to enable sufficient residence time contact between the aqueous solution with the rising DME in the column. In varying embodiments, the columns can be as short as 10 cm and as long as 30 m, for example, about 0.01 m, 0.05 m, 0.10 m, 0.5 m, 1.0 m, 1.5 m, 2.0 m, 2.5 m, 3.0 m, 3.5 m, 4.0 m, 4.5 m 5.0 m, 5.5 m, 6.0 m, 6.5 m, 7.0 m, 7.5 m, 8.0 m, 8.5 m, 9.0 m, 9.5 m, 10 m, 15 m, 20 m, 25 m or 30 m. In some embodiments, the column has a length in the range between 2 m and 5 m. As the DME moves up the column, it extracts lower alcohol from the aqueous solution. The alcohol extracted into the DME can be discharged in the column at a fluid level above the elevation of the input for the aqueous solution. In varying embodiments, the column inside diameter (ID) can be in the range of about 0.01 m to about 10 m, e.g., about 0.01 m, 0.04 m, 0.05 m, 0.08 m, 0.10 m, 0.5 m, 1 m, 1.5 m, 2 m, 2.5 m, 3 m, 3.5 m, 4 m, 4.5 m, 5 m, 6 m, 7 m, 8 m, 9 m or 10 m. In some embodiments, the ID is in the range of between about 0.04 m and about 2.0 m. In varying embodiments, the length/ID ratio is in the range of between about 5 and about 200, e.g., about 5, 10, 20, 25, 50, 75, 100, 125, 150, 175 or 200. In some embodiments, the length/ID ratio is in the range of between about 20 and about 60, e.g., about 20, 25, 30, 35, 40, 45, 50, 55 or 60. In varying embodiments, the superficial flow velocity as defined by the ratio of the total volumetric flow to the inside column area is in the range of between about 0.1 cm/sec and about 100 cm/sec, e.g., 0.1 cm/sec, 0.5 cm/sec, 1.0 cm/sec, 5 cm/sec, 10 cm/sec, 15 cm/sec, 20 cm/sec, 25 cm/sec, 50 cm/sec, 75 cm/sec, or 100 cm/sec. In some embodiments, the superficial flow velocity as defined by the ratio of the total volumetric flow to the inside column area is in the range of between about 5 to about 15 cm/sec.

Methods for performing liquid-liquid extraction ("LLE") in a countercurrent column have been well documented in the literature, e.g., by Treybal, Robert E., "Liquid Extraction," McGraw-Hill, New York, 1951). Each countercurrent stage can be implemented with a mixer and settler. As an integrated system with multiple stages, a spray tower may be used (e.g., per FIG. 10.1 in Treybal). In addition, conventional tray columns using disk and donut baffles find use (FIG. 10.4a and 10.4b in Treybal). Further, a column with random packing and flow distributor regions, using packing such as rashig rings, Pall Rings, Intalox saddles, or berl saddles, find use. In addition, a Podbielniak extractor could optionally be used (FIG. 10.12 in Treybal). Such devices are also described, e.g., in Perry's Chemical Engineering Handbook (Chapter 15, 8th edition, 2008). Columns that find use in the present extraction methods include static extraction columns, agitated extraction columns, mixer-settlers, or centrifugal extractors. Any one of these configurations can be configured to implement the desired number of stages. Economics, as constrained by throughput and equipment space constraints, would define the preferred configuration. An illustrative multistage centrifugal extractor is available from Robatel, Inc. (on the internet at rousselet-robatel.com/products/multistage-centrif-extractors-lx.php). Use of centrifugal countercurrent columns for continuous LLE is also described, e.g., on the internet at cheresources.com/centcontactor.shtml.

Extraction can be performed in one or more sequentially arranged countercurrent columns, i.e., in one or more stages. In various embodiments, the alcohol is extracted from the aqueous solution in 2, 3, 4, 5, 6, 7, 8, 9 or 10 countercurrent extraction stages (see, FIG. 2), as appropriate. In some embodiments, 5-7 countercurrent liquid-liquid extraction stages are performed, for example, 5, 6 or 7 countercurrent liquid-liquid extraction stages.

Following one or more extraction stages, the DME/alcohol stream can then pass onto a liquid recovery step, for recycling of the DME and recovery of the concentrated alcohol. In varying embodiments, the mass ratio of DME to aqueous solution is in the range of from about 0.5 to about 20, e.g., about 0.5, 1, 2, 3, 4, 5, 6, 7, 8, 9, 10, 11, 12, 13, 14, 15, 16, 17, 18, 19, or 20. In some embodiments, the mass ratio of DME to aqueous solution is in the range of from about 1 to about 3.

c. Separating the Alcohol-Saturated DME Phase and the Alcohol-Water Solution Phase After mixing DME with the dilute alcohol-water solution, the alcohol-saturated DME phase and the alcohol-water solution phase (i.e., raffinate) can be separated using any method known in the art.

For example, in embodiments where the DME is mixed with the dilute alcohol-water solution in one or more countercurrent stages of liquid-liquid extraction, the alcohol-saturated DME phase and the alcohol-water solution phase are separated upon exit of opposite ends of the countercurrent column.

In some embodiments, the alcohol-saturated DME phase and the alcohol-water solution phase naturally separate (e.g., due to a density differential) such that the phased can be physically isolated from one another, e.g., the relatively less dense alcohol-saturated DME phase can be decanted from the relatively more dense alcohol-water solution phase.

DME can be further removed or reduced from the alcohol saturated DME phase and residual DME can be removed or reduced from the alcohol-water solution phase by vaporization. This can be accomplished using any method in the art, for example, reducing pressure or heat input (flash to vaporization).

d. Recycling/Reusing Dimethyl Ether

In various embodiments, the methods further comprise the step of recovering all or part the DME from the alcohol and/or aqueous solution. This can be done using any method known in the art. For example, the DME/alcohol/water solution can be passed through a heat exchanger (i.e., vaporizer) that imparts sufficient enthalpy into the stream to enable the DME to flash to vapor upon flowing through a pressure reduction valve into a separator. Following the pressure reduction valve, a DME-dominated vapor stream and a solvent-dominated liquid stream results. The DME-dominated stream can be subsequently passed through a cooling heat exchanger (i.e., condenser) to liquify the DME. This recycled DME can be fed back to the countercurrent column for additional LLE stages, as needed or desired.

The energetics of using, reusing and recycling DME are improved by driving its vaporization and condensation using a heat pump or refrigerant circuit. This is depicted in FIG. 1. In one embodiment, the refrigerant used allows the temperature range for the DME to fluctuate from about 20° C. to about 30° C., where 20° C. is the condensation temperature and 30° C. is the flash-to-vaporization temperature. To drive this temperature difference, a heat pump with conditions that go between 15° C. and 35° C. is used. Thus, there is a 5° C. temperature difference to drive both condensation and vaporization. In this temperature range, the refrigerant R-134a finds use. At 15° C., R-134a condenses 20° C. DME and at 35° C., R-134a vaporizes 30° C. DME. In this particular case, the amount of energy to drive the DME loop is calculated to be 0.0095 kW/(kg/hr) or 9.5 kW/1000 kg/hr DME flow based on thermal balance and thermodynamic properties of the DME and R-134a.

Other temperature ranges/pressures will work, and other refrigerants, also find use. In some embodiments, the refrigerant used to drive the heat pump or refrigerant circuit is selected from R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R 406a, R-410a, R-414a, R-500, R-502, R-503, R-1301 and ammonia.

The energy expenditure of alcohol concentration from dilute aqueous solutions can be estimated from the thermodynamic properties of the alcohol solution. Energy input estimates of four test cases for the 3-fold concentration of ethanol are calculated to illustrate.

For a SF=150% (i.e., a solvent-to-feed ratio of 1.5:1) and 6 liquid-liquid-extraction ("LLE") stages, the following applies for dilute EtOH solution:
  For 2 wt % EtOH solution, the energy required is 0.903 kW-hr/kg=3249 kJ/kg=1397 BTU/lb.
  For 3 wt % EtOH solution, the energy required is 0.643 kW-hr/kg=2313 kJ/kg=995 BTU/lb
  For 3.5 wt % EtOH solution, the energy required is 0.549 kW-hr/kg=1975 kJ/kg=849 BTU/lb
  For 4 wt % EtOH solution, the energy required is 0.478 kW-hr/kg=1722 kJ/kg=740 BTU/lb With the addition of this energy, the concentration of the EtOH is increased by roughly a factor of 3. This means that an aqueous solution comprising about 3 wt % EtOH is concentrated to an aqueous solution comprising about 9 wt % EtOH; an aqueous solution comprising about 3.5 wt % EtOH is concentrated to an aqueous solution comprising about 10.5 wt % EtOH; and an aqueous solution comprising about 4 wt % EtOH is concentrated to an aqueous solution comprising about 12 wt % EtOH. This increase in concentration via DME LLE is much more energetically and economically efficient than using distillation over the same concentration ranges. Distillation energy would require between about 2 and 10 times greater energy input than the present DME extraction methods.

Concentrated EtOH can be separated or isolated and subject to further concentration, e.g., using other techniques. For example, distillation can be used to boost the ethanol content to concentrations above the higher concentration, e.g., from about 10% to approximately 90 wt % or more, wherein at higher concentrations molecular sieves become practical for increasing the EtOH to nearly anhydrous level.

In addition, the DME LLE can be applied to concentrating butanol and/or ethanol from ABE solution. Energy input estimates of two test cases are calculated to illustrate:
  For 1 wt % BuOH solution, SF=100% (i.e., a solvent-to-feed ratio of 1:1), and 8 LLE stages, the energy required is 1.092 kW-hr/kg=3932 kJ/kg=1691 BTU/lb
  For 2 wt % BuOH solution, SF=140% (i.e., a solvent-to-feed ratio of 1.4:1), and 6 LLE stages, the energy required is 0.698 kW-hr/kg=2514 kJ/kg=1081 BTU/lb In the case of butanol, DME LLE achieves an increase in concentration of approximately 4-fold. This means that an aqueous solution comprising about 1 wt % BuOH is concentrated to an aqueous solution comprising about 4 wt % BuOH. An aqueous solution comprising about 2 wt % BuOH, is concentrated to an aqueous solution comprising about 8 wt % BuOH. BuOH has a limited solubility in water of approximately 7 wt %. This means when concentrated to about 8 wt %, a portion of BuOH would form a second, BuOH-rich phase that can be physically decanted from the water. This forms a highly efficient approach for separating BuOH from aqueous solution.

In the process of extracting the BuOH, both acetone and ethanol would also be extracted. Subsequent distillation of the BuOH/acetone/ethanol mixture could be used to achieve pure streams; however, the amount of water would be substantially reduced. DME LLE provides for an improved energy efficiency versus conventional distillation of the dilute ABE solution or adsorption-distillation—the current benchmark process for energy efficient separation of BuOH from dilute solution. Distillation requires between 2 and 10 times more energy input than the DME LLE method.

In other embodiments, the DME is condensed using vapor recompression. Vapor recompression is simpler and is commonly used in the oil and gas industries. However, implementing vapor recompression requires a compressor of specific design for use with flammable media (i.e., DME). Use of a refrigerant circuit has the advantage that it can be implemented with commercial off-the-shelf refrigerant equipment (e.g., refrigerant compressors, expansion valves, heat exchangers).

e. Separating/Isolating Concentrated Alcohol

DME concentration of the alcohol from the aqueous solution can proceed in a continuous and iterative manner until a desired threshold concentration is achieved. The threshold concentration can be based on the starting concentration of alcohol in the feedstock material, for example, the threshold concentration may be 1-fold, 2-fold, 3-fold, 4-fold, 5-fold, or greater, in comparison to the concentration of the alcohol in the feedstock material. In various embodiments, the threshold concentration is a target concentration of alcohol in the aqueous solution, for example, 7 wt %, 8 wt %, 9 wt %, 10 wt %, 11 wt %, 12 wt %, 13 wt %, 14 wt % or 15 wt % alcohol.

Once a threshold concentration level of the alcohol is achieved, the concentrated alcohol can be isolated. This can be done using any method known in the art. As discussed above, the alcohol can be released from the DME by vaporizing the liquid phase DME. The alcohol may be subject to further concentration procedures, e.g., by distillation. Depending on the composition of the starting feedstock material, the DME may co-concentrate other compounds with the alcohol. The alcohol can be purified or separated from such compounds, as needed or desired, using methods known in the art.

f. Illustrative Embodiments i. Concentration of Dilute Ethanol (EtOH) Aqueous Solutions One illustrative embodiment for the concentration of dilute concentrations of ethanol from an aqueous solution, e.g, a fermentation broth, is provided in FIG. 1. An aqueous solution, e.g, a fermentation broth, comprising less than about 5% ethanol (e.g., from about 0.1% to about 3% ethanol) is contacted with liquid phase DME at about a 1.5:1 solvent to feed ratio in a countercurrent column maintained at a pressure of about 8 bar and at a temperature of about 38° C. The DME is mixed with the dilute EtOH aqueous solution in sequential countercurrent columns, extracting the EtOH into the DME over 5-7 liquid-liquid extraction stages.

The aqueous phase comprising DME saturated with EtOH is delivered to a flash column and exposed to a flash temperature in the range of about 110-130° C. to remove the DME by vaporization. The vaporized DME is condensed back to liquid phase for recycling and reuse. The vaporization and condensation of DME is driven by a refrigeration circuit, e.g., using the refrigerant R134a. Residual DME remaining in the concentrated EtOH after flash vaporization can be removed by distillation. Under these parameters, it is possible achieve about 50-60% recovery and a 3-fold concentration of the EtOH from the feedstock aqueous solution with an energy input of less than about 1500 BTU/lb EtOH recovered, for example, less than about 1000 BTU/lb EtOH recovered.

DME is recovered from the aqueous phase comprising unextracted EtOH (i.e., the raffinate) by reducing pressure (e.g., to about 300 torr; 0.4 atm; 0.4 bar; 5.8 psi), thereby vaporizing the DME in the aqueous raffinate. Residual DME in the aqueous raffinate, about 6%, can be returned to the fermenter (after sterilization). Raffinate returned to the fermentation medium comprises a portion of the total fermentation medium such that the total concentration of DME in the fermentation medium is less than 3 wt. %, for example less than 2 wt. % or less than 1 wt. %.

ii. Concentration of Dilute Butanol (BuOH) Aqueous Solutions

Figure 2:
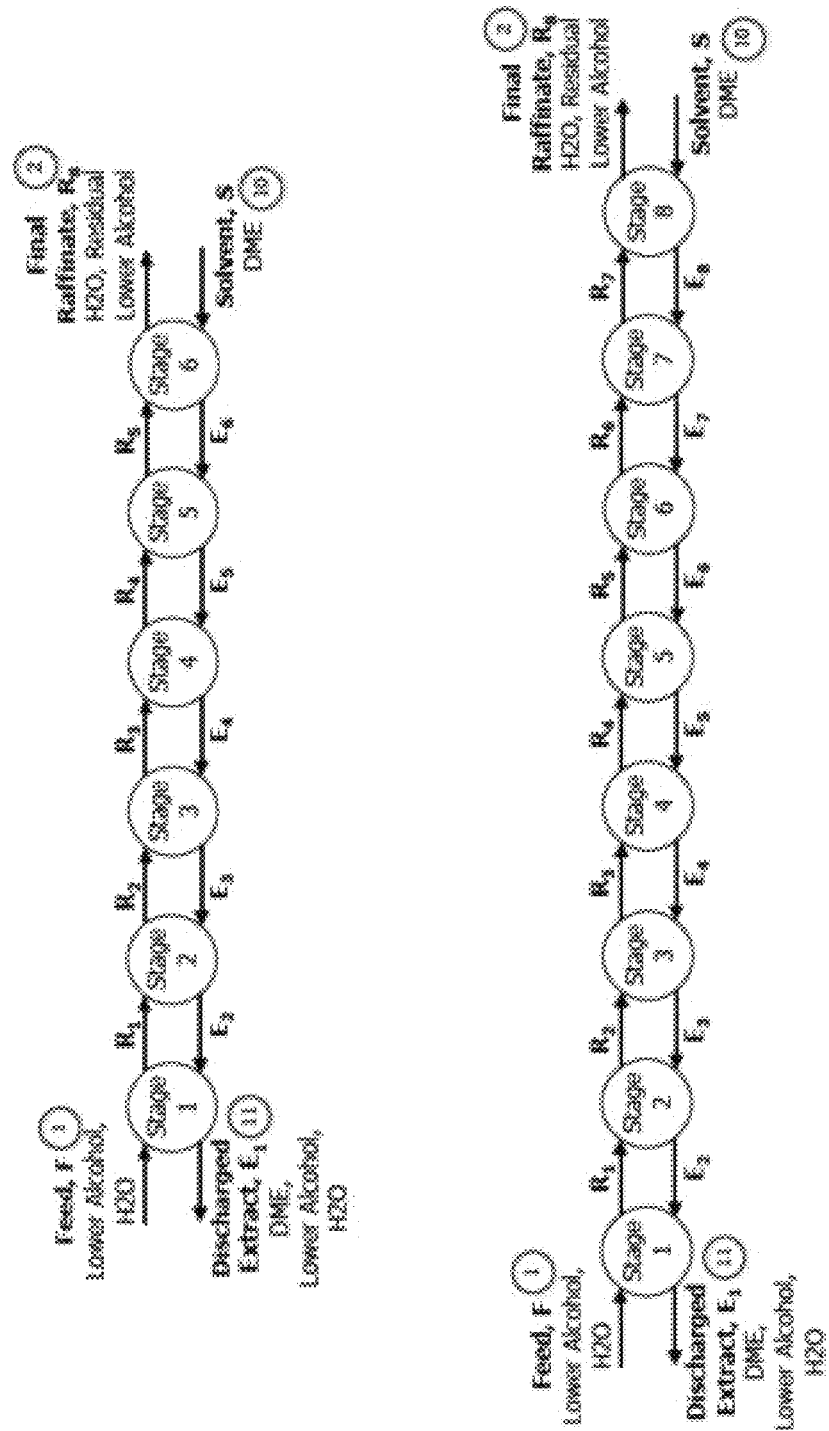
FIG. 2 illustrates a schematic for multistage countercurrent LLE.

One illustrative embodiment for the concentration of dilute concentrations of butanol from an aqueous solution, e.g, a fermentation broth, is provided in FIG. 2. An aqueous solution, e.g, a fermentation broth, comprising less than about 5% butanol (e.g., from about 0.1% to about 3% butanol) is contacted with liquid phase DME at about a 1.0:1 solvent to feed ratio in a countercurrent column maintained at a pressure of about 8 bar and at a temperature of about 38° C. The DME is mixed with the dilute BuOH aqueous solution in sequential countercurrent columns, extracting the BuOH into the DME over 5-7 liquid-liquid extraction stages.

The aqueous phase comprising DME saturated with BuOH is delivered to a flash column and exposed to a flash temperature in the range of about 110-130° C. to remove the DME by vaporization. The vaporized DME is condensed back to liquid phase for recycling and reuse. The vaporization and condensation of DME is driven by a refrigeration circuit, e.g., using the refrigerant R134a. Residual DME remaining in the concentrated BuOH after flash vaporization can be removed by distillation. Under these parameters, it is possible achieve greater than 90% recovery and a 15-fold concentration of the BuOH from the feedstock aqueous solution with an energy input of less than about 3000 BTU/lb BuOH recovered, for example, less than about 2900 BTU/lb BuOH recovered, for example, an energy input in the range of about 2400-2900 BTU/lb BuOH recovered.

DME is recovered from the aqueous phase comprising unextracted BuOH (i.e., the raffinate) by reducing pressure (e.g., to about 300 torr; 0.4 atm; 0.4 bar; 5.8 psi), thereby vaporizing the DME in the aqueous raffinate. Residual DME in the aqueous raffinate, about 6%, can be returned to the fermenter (after sterilization). Raffinate returned to the fermentation medium comprises a portion of the total fermentation medium such that the total concentration of DME in the fermentation medium is less than 3 wt. %, for example less than 2 wt. % or less than 1 wt. %.

3. Systems for Extracting Lower Alcohols from Dilute Aqueous Solution

FIG. 1 shows one embodiment of a system for extracting a lower alcohol from a dilute alcohol-water solution. The system comprises a liquid feed inlet for receiving the alcohol-water solution, an extraction vessel configured to extract the alcohol with DME, a vaporizer for converting the DME to vapor phase, a collector configured to receive the concentrated alcohol, a condenser for converting the vapor phase DME back to liquid phase, and a refrigerant circuit to drive the vaporization and condensation of DME in an energetically efficient manner.

The system of the present invention extracts alcohol from a dilute alcohol-water solution comprising less than 10 wt. % alcohol, e.g., in the range of about 0.1 wt. % to about 10 wt. % alcohol. In preferred embodiments, the systems of the invention allow for a continuous flow process, wherein materials are continuously flowing from one step of the system to the next. The systems preferably allow for the recycling and reuse of the DME solvent, and multiple iterations or stages of alcohol concentration to achieve an aqueous solution with an alcohol concentration greater than a target threshold concentration. The recycling and reuse of materials provides several energy savings. Additional energy savings stem from the lack of a distillation step in the concentration of dilute concentrations of lower alcohol. Instead of an energy inefficient process such as distillation, the present invention uses liquid DME to extract the alcohol. The DME-containing alcohol is then vaporized to separate the alcohol, followed by recondensation of the DME in order to recycle and reuse the DME. Accordingly, the system of the present invention provides an energy efficient process for extracting lower alcohols from a dilute alcohol-water solution.

As discussed above, the alcohol-water solution can be a fermentation broth or beer, for example, from the fermentation of fruits and/or vegetables, or an ABE solution. In particular, corn is useful to prepare the fermentation broth of the present invention. In this case, ethanol is extracted from the ethanol-water solution using DME.

The dilute alcohol-water solution is provided to the system of the present invention via a liquid feed inlet, for example, piping, hosing, tubing or reservoirs. One of skill in the art will appreciate that other input means find use. The alcohol-water solution can be fresh feedstock, for example, from the fermentation broth, and/or can be from recycling alcohol-water solution that has been subject to at least one iteration of concentration.

The feedstock alcohol-water solution is placed in an extraction vessel where the alcohol-water solution is contacted with liquid phase DME. The DME is in a phase such that the distribution coefficient for alcohol in the alcohol-water solution favors the transfer of the alcohol from the water to the DME, thereby facilitating extraction and concentration of the alcohol in the DME. The phase of the DME can be controlled by the appropriate selection of temperature and pressure. In preferred embodiments, the liquid phase DME is used at a pressure and temperature that is not close to the critical point for DME (53.405 bar and 127.15° C.). In some embodiments, DME extraction and concentration of alcohol is performed at a temperature in the range of about 20° C. to about 35° C. and at a superambient pressure of less than 10 bar, for example in the range of about 3 to 5 bar.

The alcohol is extracted into the DME using any known means in the art. For example, the alcohol can be extracted by the DME using countercurrent column (CC) liquid-liquid extraction (LLE). Within the CC, one can consider that three processes are occurring in conjunction: mixing, coalescing, and separation. Mixing of the phases allows the interface between them to have a large area, and the analyte can move between the phases according to its partition coefficient. Within the countercurrent column, the alcohol-water phase moves down the column and the DME-rich phase rises within the column. After passage through the countercurrent column, the alcohol-water phase has been partially depleted of alcohol and the DME-rich phase has been enriched with alcohol. The depleted alcohol-water phase can be returned for blending with feedstock dilute alcohol solution. All or a portion of the alcohol-enriched DME-rich phase can be subject to vaporization to separate the alcohol from the DME. In some embodiments, this DME stream can be reintroduced into the column through a reflux valve. The recycling of the DME allows the DME to be reused and increases the efficient use of the DME.

The DME is then separated from the alcohol in a vaporizer, by converting the DME to the vapor phase and collecting concentrated alcohol in water in a collector. Vaporization is accomplished by changing the temperature and pressure in order to change the DME from the liquid phase to the vapor phase.

DME that has been vaporized can be recycled by first condensing the vaporized DME using a condenser by again changing the temperature and pressure in order to change the DME from vapor phase to liquid phase. Condensation of the DME is followed by reinjecting the DME into the extraction vessel. The recycling of the DME allows the DME to be reused, and minimizes the energy required for the extraction by minimizing materials used and energy consumed. The inclusion of a heat pump or refrigerant circuit to drive the vaporization and condensation of DME provides added energy efficiencies in the recycling and reuse of DME.

EXAMPLES

The following examples are offered to illustrate, but not to limit the claimed invention.

Example 1

Extraction of Dilute Ethanol and Acetone-Butanol-Ethanol (ABE) from Aqueous Solution Using Liquid Phase Dimethyl Ether (DME)

Experimental Set-up

This example shows the effectiveness of liquid dimethyl ether to remove ethanol from water at initial concentrations of 2% and 4%, and in another test to remove acetone-butanol-ethanol from a typical "ABE" solution.

The tests were carried out in a 50-inch long by 0.68-inch internal diameter (ID) column containing stainless steel distillation packing to increase mass transfer between the liquid DME and the aqueous solution. The flow rate of the liquid DME for all the tests was about 20 SL/min, which calculates to a superficial velocity of the liquid DME of ~0.3 cm/sec.

Figure 3:
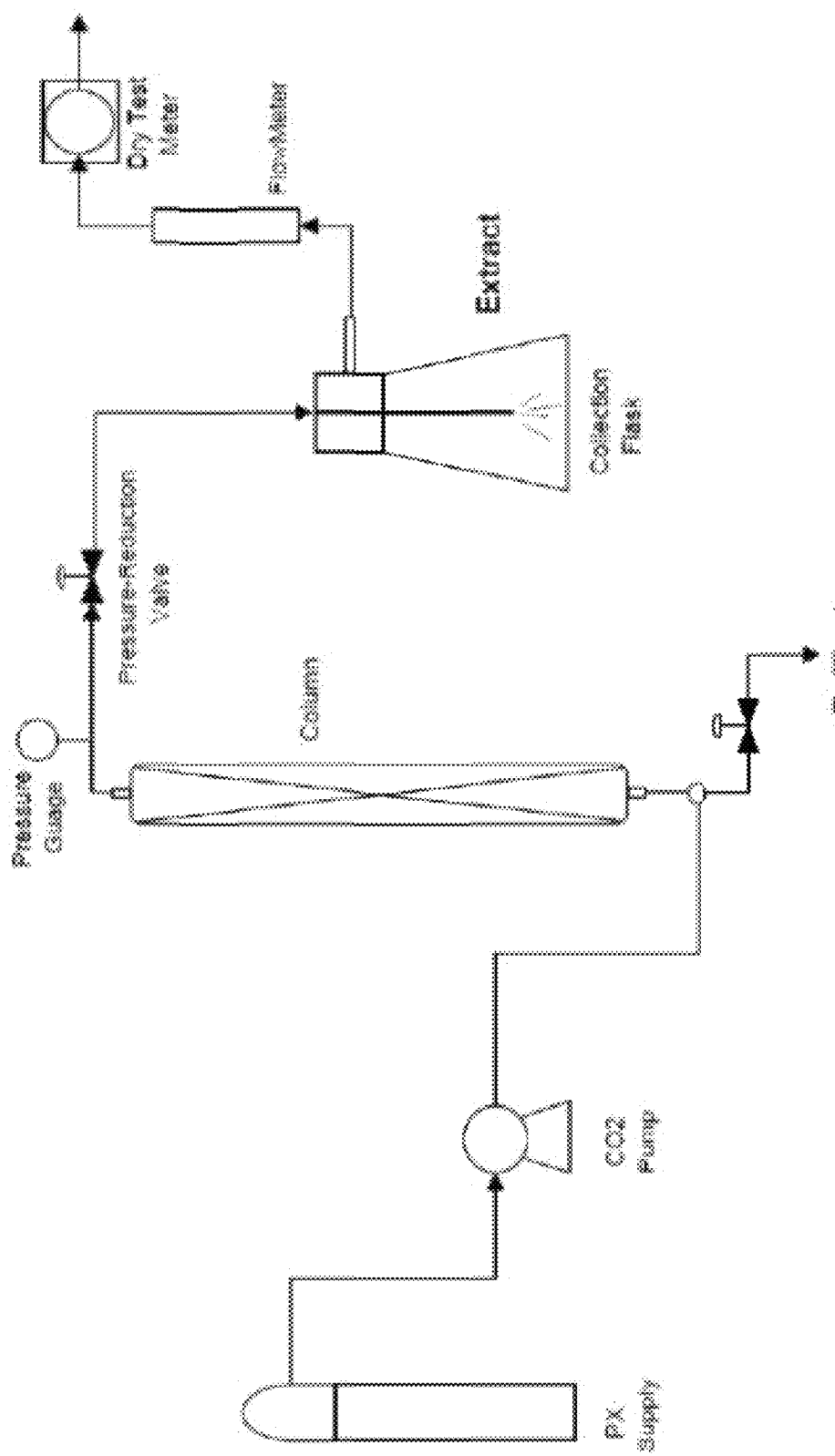
FIG. 3 illustrates a simplified set-up of the equipment used in Example 1.
Figure 4:
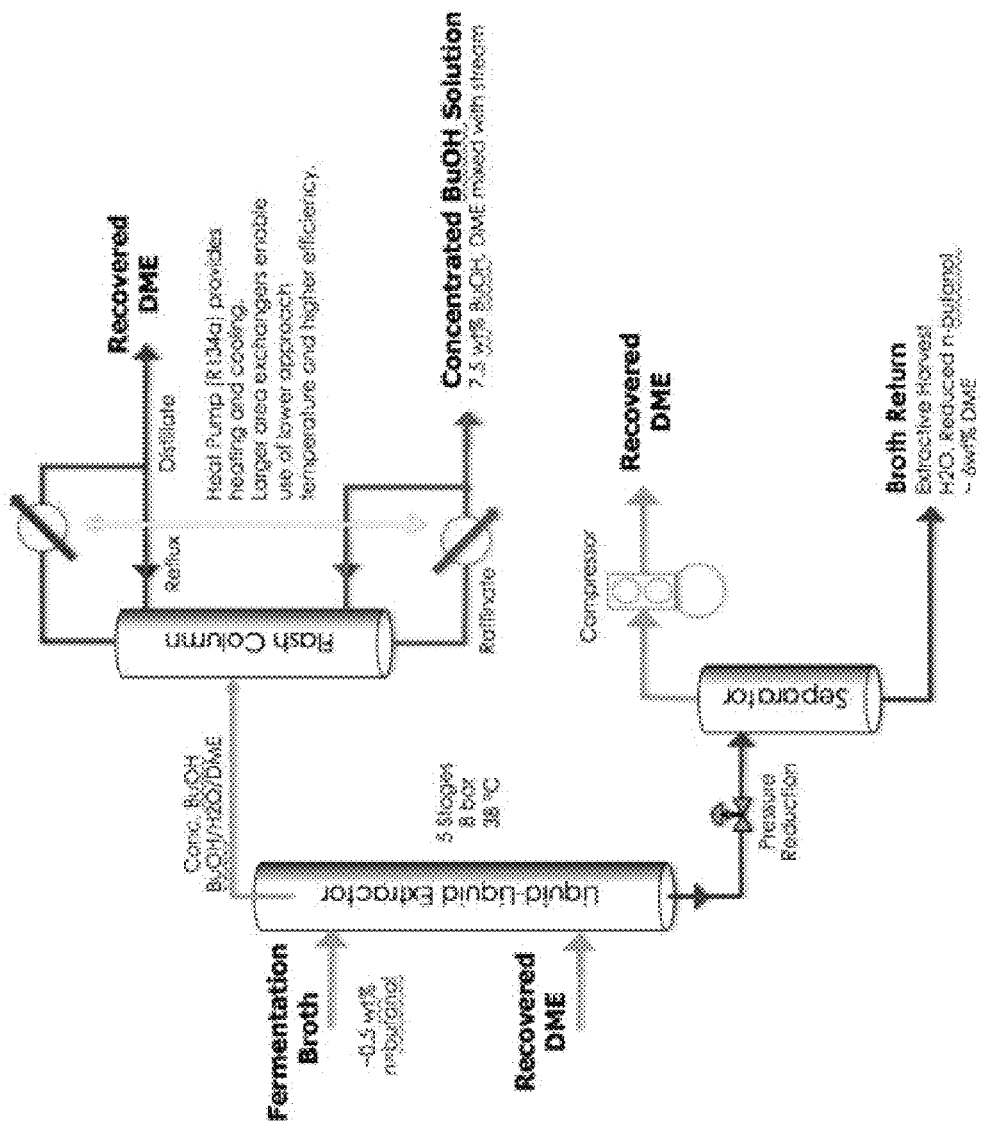
FIG. 4 illustrates a schematic for continuous flow, energy efficient concentration of lower alcohols (e.g., butanol) from aqueous solution using DME liquid-liquid-extraction. In relation to the schematic of FIG. 1, this schematic shows the downstream operations from the LLE (Liquid-liquid extraction) column to separate the liquid from the DME vapor. This schematic shows an embodiment where the heat pump would be employed (e.g., for recovering the DME from the concentrated BuOH stream).

FIG. 3 shows the simplified schematic set up of the equipment used for the tests summarized in this example.

For each test, about 65 g of a pre-made feed solution was charged to the extraction column, and the column was sealed. DME was introduced into the system and pressure was maintained at 250 psi with the lab pump. Each run was carried out at ambient temperature (about 30° C.), and flow was manually controlled with the pressure-reduction valve.

About ⅓ of the charge was extracted in each test with DME in three fractions, and the raffinate was collected at the end of each test in two fractions. In the event that the concentration of ethanol, or ABE, in the raffinate was not homogeneous along the length of the column, the raffinate was collected in two fractions where RAF#1 was the first (bottom) portion of the raffinate drained and RAF#2 was the remaining (upper) portion.

All samples along with controls were sent to R.D. Laboratories (Wash., MO) for gas chromatography (GC) analysis.

Results and Discussion

Two tests were carried out with ethanol-water solutions with ethanol at 2 wt % and 4 wt % concentrations in the feed. The tables below show the material balance and analytical results for each test.

TABLE 1

2 wt % Ethanol Feed Concentration

| Fraction | Wt (g) | Wt % of charge | DME (g) | Wt % Solubility (w/w extract/DME) | Incremental S/F | Conc. Ethanol (wt %) |
|---|---|---|---|---|---|---|
| Control (Charge) | 64.7 | — | — | — | — | 2.15* |
| F1 | 7.79 | 12.0 | 84 | 9.2 | 1.3 | 6.63 |
| F2 | 5.84 | 9.0 | 56 | 10.4 | 0.9 | 5.57 |
| F3 | 5.98 | 9.2 | 56 | 10.7 | 0.9 | 3.19 |
| RAF 1 | 13.3 | 20.6 | — | — | — | 0.06 |
| RAF 2 | 26.8 | 41.4 | — | — | — | 0.13 |
| % Total Recovery: | | 92.2 | | | | |

*The weighed concentration of the feed was 2.16 wt %

TABLE 2

4 wt % Ethanol Feed Concentration

| Fraction | Wt (g) | Wt % of charge | DME (g) | Wt % Solubility (w/w extract/DME) | Incremental S/F | Conc. Ethanol (wt %) |
|---|---|---|---|---|---|---|
| Control (Charge) | 65.4 | — | — | — | — | 4.04* |
| F1 | 11.21 | 17.1 | 84 | 13.3 | 1.3 | 11.11 |
| F2 | 6.45 | 9.9 | 56 | 11.5 | 0.9 | 7.73 |
| F3 | 6.75 | 10.3 | 56 | 12.1 | 0.9 | 3.94 |
| RAF 1 | 16.97 | 25.9 | — | — | — | 0.06 |
| RAF 2 | 11.85 | 18.1 | — | — | — | 0.10 |
| % Total Recovery: | | 81.3 | | | | |

*The weighed concentration of the feed was 4.20 wt %

TABLE 3

Acetone-Butanol-Ethanol Feed Solution

| | | | | | | GC analysis (wt %) | | |
|---|---|---|---|---|---|---|---|---|
| Fraction | Wt (g) | Wt % of charge | DME (g) | Wt % Solubility (w/w extract/DME) | Incremental S/F | A acetone | B butanol | E ethanol |
| Control (Charge) | 71.66 | — | — | — | — | 0.21 | 0.50 | 0.09 |
| F1 | 6.7 | 9.3 | 75 | 8.9 | 1.0 | 0.52 | 2.91 | 0.40 |
| F2 | 5.19 | 7.2 | 56 | 9.3 | 0.8 | 0.31 | 0.84 | 0.29 |
| F3 | 5.47 | 7.6 | 56 | 9.7 | 0.8 | 0.08 | 0.10 | 0.15 |
| RAF 1 | 15.62 | 21.8 | — | — | — | ND | ND | ND |
| RAF 2 | 33.95 | 47.3 | — | — | — | ND | ND | ND |
| % Total Recovery: | | 93.2 | | | | | | |

*The weighed concentration of the feed: A = 0.022 wt %, B = 0.050 wt %, E = 0.11 wt %.

The distribution coefficient (DC) is calculated as the ratio of the concentration of the component in the extract (y) phase to the concentration of the component in the raffinate (x) phase, or $DC = Cy/Cx$. Using the material balance information in the tables above, and the component analysis supplied by R.D. Labs, the incremental DCs for each fraction were calculated. These DCs are calculated using the conservative assumption that there is no dissolved DME in the liquid phase remaining in the extractor. The DCs would increase by about 30% if it was assumed that the liquid phase in the extractor has about 30% dissolved DME.

The table below shows the calculated DCs for each fraction from the 2% EtOH and 4% EtOH tests.

TABLE 4

DC for Ethanol Solutions Extracted with Liquid DME

| Test | Fraction | Distribution Coefficient |
|---|---|---|
| 2% EtOH | F1 | 0.37 |
| 2% EtOH | F2 | 0.49 |
| 2% EtOH | F3 | 0.39 |
| 4% EtOH | F1 | 0.51 |
| 4% EtOH | F2 | 0.42 |
| 4% EtOH | F3 | 0.27 |

The following table shows the calculated DCs for each fraction and each of the three components from the ABE extraction test.

TABLE 5

DCs for ABE Solution Extracted with Liquid DME

| | Distribution Coefficient | | |
|---|---|---|---|
| Fraction | Acetone | Butanol | Ethanol |
| F1 | 0.24 | 0.95 | 0.57 |
| F2 | 0.16 | 0.36 | 0.65 |
| F3 | 0.04 | 0.04 | 0.50 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An energetically efficient method for concentrating a C2-C6 alcohol from a dilute alcohol-water solution comprising:
   a) mixing the dilute alcohol-water solution with liquid phase dimethyl ether (DME), wherein the distribution coefficient for the alcohol in a mixture of the DME and the alcohol-water solution favors the transfer of the alcohol from the alcohol-water solution to the DME, thereby yielding a solution comprising a first phase and a second phase, the first phase comprising alcohol-saturated DME and the second phase comprising the dilute alcohol-water solution, thereby extracting a portion of the alcohol from the alcohol-water solution into the DME;
   b) separating the first phase and the second phase;
   c) vaporizing the liquid phase DME in the first phase to vapor phase DME, thereby releasing the alcohol from the DME, yielding a concentrated alcohol-water solution;
   d) recovering the vapor phase DME by condensing to liquid phase, wherein the vaporizing and the condensing of the DME is driven by a refrigerant circuit; and
   e) repeating steps a)-d), wherein the DME recovered in step d) is mixed with the dilute alcohol-water solution in step a).

2. The method of claim 1, further comprising the step of isolating the alcohol from the concentrated alcohol-water solution released from the DME.

3. The method of claim 1, wherein the mixing of step a) is performed in one or more countercurrent extraction stages.

4. The method of claim 1, wherein the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301 and ammonia.

5. The method of claim 1, wherein the steps are performed as a continuous flow process.

6. The method of claim 1, wherein steps a)-d) are repeated 10 or fewer times.

7. The method of claim 1, wherein the feedstock dilute alcohol-water solution comprises from about 0.1 wt. % to about 5.0 wt. % alcohol.

8. The method of claim 1, wherein the feedstock dilute alcohol-water solution comprises cellular biomass in suspension.

9. The method of claim 1, wherein the alcohol is concentrated to a concentration of at least 7 wt. % alcohol.

10. The method of claim 1, wherein the method does not comprise distillation.

11. The method of claim 1, wherein the method is performed a temperature in the range of about 20° C. to about 150° C.

12. The method of claim 1, wherein the method is performed at a pressure in the range of about 3 bar to about 50 bar.

13. The method of claim 1, wherein the C2-C6 alcohol is selected from ethanol, a propanol, a butanol, a pentanol and a hexanol.

14. The method of claim 1, wherein the alcohol is concentrated at least 3 fold.

15. The method of claim 1, wherein the dilute alcohol-water solution is a fermentation beer or fermentation broth.

16. The method of claim 15, wherein the fermentation beer or fermentation broth comprises up to about 3 wt. % DME.

17. A method for concentrating a C2-C6 alcohol from a dilute alcohol-water solution comprising:
   a) mixing the dilute alcohol-water solution with liquid phase dimethyl ether (DME), wherein the distribution coefficient for the alcohol in a mixture of the DME and the alcohol-water solution favors the transfer of the alcohol from the alcohol-water solution to the DME, thereby yielding a solution comprising a first phase and a second phase, the first phase comprising alcohol-saturated DME and the second phase comprising the dilute alcohol-water solution, thereby extracting a portion of the alcohol from the alcohol-water solution into the DME;
   b) separating the first phase and the second phase; and
   c) converting the liquid-phase DME to vapor phase, thereby releasing the alcohol from the DME, yielding a concentrated alcohol-water solution.

18. The method of claim 17, wherein the mixing of step a) is performed in one or more countercurrent extraction stages.

19. The method of claim 17, further comprising the step of recycling the vapor phase DME produced in step c).

20. The method of claim 17, wherein the DME is recycled by vaporizing and the condensing, wherein the vaporizing and the condensing of the DME is driven by a refrigerant circuit.

21. The method of claim 17, wherein the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301 and ammonia.

22. The method of claim 17, wherein the steps are performed as a continuous flow process.

23. The method of claim 17, comprising repeating steps a)-c) two or more times.

24. The method of claim 17, wherein the feedstock dilute alcohol-water solution comprises from about 0.1 wt. % to about 5.0 wt. % alcohol.

25. The method of claim 17, wherein the feedstock dilute alcohol-water solution comprises cellular biomass in suspension.

26. The method of claim 17, wherein the alcohol is concentrated to a concentration of at least 7 wt. % alcohol.

27. The method of claim 17, wherein the method does not comprise distillation.

28. The method of claim 17, wherein the method is performed a temperature in the range of about 20° C. to about 150° C.

29. The method of claim 17, wherein the method is performed at a pressure in the range of about 3 bar to about 50 bar.

30. The method of claim 17, wherein the C2-C6 alcohol is selected from ethanol, a propanol, a butanol, a pentanol and a hexanol.

31. The method of claim 17, wherein the alcohol is concentrated at least 3 fold.

32. The method of claim 17, wherein the dilute alcohol-water solution is a fermentation beer or fermentation broth.

33. The method of claim 32, wherein the fermentation beer or fermentation broth comprises up to about 3 wt. % DME.

* * * * *

UNITED STATES PATENT AND TRADEMARK OFFICE
CERTIFICATE OF CORRECTION

PATENT NO. : 9,029,615 B2  
APPLICATION NO. : 13/801901  
DATED : May 12, 2015  
INVENTOR(S) : Schonemann et al.

Page 1 of 1

It is certified that error appears in the above-identified patent and that said Letters Patent is hereby corrected as shown below:

On the title page item (72), line 9, change "Kenneth Square" to -- Kennett Square --

In the claims

Column 21, line 53 claim 11, line 2 change "a temperature" to -- at a temperature --

Column 22, line 50 claim 28, line 2 change "a temperature" to -- at a temperature --

Signed and Sealed this
Sixteenth Day of August, 2016

Michelle K. Lee
*Director of the United States Patent and Trademark Office*